(12) United States Patent
Tsujiko et al.

(10) Patent No.: US 10,586,973 B2
(45) Date of Patent: Mar. 10, 2020

(54) METHOD OF PRODUCING SECONDARY BATTERY

(71) Applicant: TOYOTA JIDOSHA KABUSHIKI KAISHA, Toyota-shi, Aichi-ken (JP)

(72) Inventors: Akira Tsujiko, Miyoshi (JP); Ippei Goto, Toyota (JP)

(73) Assignee: TOYOTA JIDOSHA KABUSHIKI KAISHA, Toyota (JP)

(*) Notice: Subject to any disclaimer, the term of this patent is extended or adjusted under 35 U.S.C. 154(b) by 74 days.

(21) Appl. No.: 15/811,021

(22) Filed: Nov. 13, 2017

(65) Prior Publication Data

US 2018/0145308 A1     May 24, 2018

(30) Foreign Application Priority Data

Nov. 24, 2016   (JP) ................. 2016-227775

(51) Int. Cl.

| | | |
|---|---|---|
| *H01M 4/02* | (2006.01) | |
| *H01M 4/131* | (2010.01) | |
| *H01M 4/04* | (2006.01) | |
| *H01M 10/44* | (2006.01) | |
| *G01N 29/04* | (2006.01) | |

(Continued)

(52) U.S. Cl.
CPC ............ *H01M 4/02* (2013.01); *G01N 29/043* (2013.01); *H01M 4/0404* (2013.01); *H01M 4/131* (2013.01); *H01M 4/505* (2013.01); *H01M 10/446* (2013.01); *H01M 10/0525* (2013.01); *H01M 2004/021* (2013.01); *H01M 2004/028* (2013.01)

(58) Field of Classification Search
CPC ...... H01M 4/02; H01M 4/0404; H01M 4/131; H01M 4/505; H01M 10/446; H01M 10/0525
See application file for complete search history.

(56) References Cited

U.S. PATENT DOCUMENTS 5,932,991 A * 8/1999 Ahuja ............... H01M 10/4214
                                                  320/137
2013/0314051 A1* 11/2013 Takezawa ......... H01M 10/0525
                                                  320/134

FOREIGN PATENT DOCUMENTS

| JP | 2002-298927 A | 10/2002 |
|---|---|---|
| JP | 2015-153484 A | 8/2015 |
| JP | 2015-215279 A | 12/2015 |

* cited by examiner

*Primary Examiner* — Jimmy Vo
(74) *Attorney, Agent, or Firm* — Oliff PLC (57) ABSTRACT

A method of producing a secondary battery disclosed here includes forming a positive electrode active material layer containing a lithium- and manganese-containing composite oxide on a positive electrode current collector to produce a positive electrode; measuring a peel strength between the positive electrode active material layer and the positive electrode current collector; producing a secondary battery assembly including the positive electrode, a negative electrode, and a nonaqueous electrolyte using the positive electrode; and initially charging the secondary battery assembly. When the secondary battery assembly is initially charged, a charging rate is determined based on the measured peel strength, and in a predetermined peel strength range, a lower charging rate is set for a secondary battery assembly including a positive electrode having a low peel strength than for a secondary battery assembly including a positive electrode having a large peel strength.

6 Claims, 6 Drawing Sheets

(51) Int. Cl.
*H01M 4/505* (2010.01)
*H01M 10/0525* (2010.01)

METHOD OF PRODUCING SECONDARY BATTERY

INCORPORATION BY REFERENCE

The disclosure of Japanese Patent Application No. 2016-227775 filed on Nov. 24, 2016 including the specification, drawings and abstract is incorporated herein by reference in its entirety.

BACKGROUND

1. Technical Field

The present disclosure relates to a method of producing a secondary battery.

2. Description of Related Art

Nonaqueous electrolyte secondary batteries such as lithium ion secondary batteries (lithium secondary batteries) are lighter in weight and have a higher energy density than batteries of the related art. Therefore, they have recently been used as a so-called portable power supply for a computer and a mobile terminal and a power supply for driving a vehicle. In particular, lightweight lithium ion secondary batteries capable of obtaining a high energy density are expected to be increasingly applied as high output power supplies for driving vehicles such as an electric vehicle (EV), a hybrid vehicle (HV), and a plug-in hybrid vehicle (PHV).

A typical configuration of a lithium ion secondary battery includes a positive electrode, a negative electrode, and a nonaqueous electrolyte. A typical configuration of the positive electrode includes a positive electrode current collector and a positive electrode active material layer provided on the positive electrode current collector. As a positive electrode active material contained in the positive electrode active material layer, a composite oxide containing lithium and manganese such as a spinel type lithium and manganese composite oxide and a composite oxide in which another metal element is additionally added to a spinel type lithium and manganese composite oxide are frequently used (for example, refer to Japanese Unexamined Patent Application Publication No. 2002-298927(JP 2002-298927 A)).

SUMMARY

The inventors conducted research and found that, when a secondary battery is produced using a positive electrode including a positive electrode active material layer containing a lithium- and manganese-containing composite oxide, if a secondary battery is produced using a positive electrode having a low peel strength between a positive electrode active material layer and a positive electrode current collector, a capacity of the obtained secondary battery is low. The peel strength between the positive electrode active material layer and the positive electrode current collector is influenced by a mixing state of a composition for forming a positive electrode active material layer containing a positive electrode active material, a binder, and the like, and it is difficult completely control the mixing state. Therefore, produced positive electrodes may be mixed with positive electrodes having a low peel strength between the positive electrode active material layer and the positive electrode current collector. Currently, such a positive electrode having a low peel strength between the positive electrode active material layer and the positive electrode current collector has to be discarded. Therefore, there is room for improvement in the yield of production of a secondary battery.

Here, the present disclosure provides a method through which it is possible to produce a secondary battery with a high yield using a positive electrode including a positive electrode active material layer containing a lithium- and manganese-containing composite oxide.

It is known that, in a secondary battery in which a composite oxide containing lithium and manganese (hereinafter referred to as a "lithium- and manganese-containing composite oxide") is used as a positive electrode active material, manganese is eluted from the lithium- and manganese-containing composite oxide, and thus the battery capacity is reduced. The inventors developed the idea that, in a positive electrode having a low peel strength between a positive electrode active material layer and a positive electrode current collector, there are relatively many portions in which the positive electrode active material layer and the positive electrode current collector are not in close contact with each other, and thought that manganese is likely to be eluted from the lithium- and manganese-containing composite oxide in those portions, and thus completed the present disclosure.

A first method of producing a secondary battery disclosed here includes forming a positive electrode active material layer containing a lithium- and manganese-containing composite oxide on a positive electrode current collector to produce a positive electrode; measuring a peel strength between the positive electrode active material layer and the positive electrode current collector; producing a secondary battery assembly including the positive electrode, a negative electrode, and a nonaqueous electrolyte using the positive electrode; and initially charging the secondary battery assembly, wherein, when the secondary battery assembly is initially charged, a charging rate is determined based on the measured peel strength, and in a predetermined peel strength range, a lower charging rate is set for a secondary battery assembly including a positive electrode having a low peel strength than for a secondary battery assembly including a positive electrode having a large peel strength.

In such a configuration, in the lithium ion secondary battery including a positive electrode having a low peel strength between the positive electrode active material layer and the positive electrode current collector, when the charging rate is changed, it is possible to prevent the lithium- and manganese-containing composite oxide which is a positive electrode active material from being exposed to an acid (particularly, HF) generated during initial charging without increasing the valence of manganese. Accordingly, it is possible to prevent low-valence manganese from being eluted from the lithium- and manganese-containing composite oxide. Thus, it is also possible to produce the secondary battery using a positive electrode having a low peel strength between the positive electrode active material layer and the positive electrode current collector which was discarded in the related art. Therefore, it is possible to reduce the number of positive electrodes to be discarded and as a result, it is possible to produce the secondary battery with a high yield.

In one form of the first method of producing a secondary battery disclosed here, when the secondary battery assembly is initially charged, ultrasonic waves may be emitted toward an interface between the positive electrode active material layer and the positive electrode current collector, and the charging rate may be changed according to a transmission intensity of the ultrasonic waves.

In such a configuration, it is possible to further optimize the charging rate in the initial charging process.

In one form of the first method of producing a secondary battery disclosed here, when a transmission intensity of the ultrasonic waves is equal to or less than a predetermined value, the charging rate may be reduced.

In one form of the first method of producing a secondary battery disclosed here, charging rate≤a×peel strength$^2$+b, wherein a>0, b≈0.

In one form of the first method of producing a secondary battery disclosed here, charging rate=a×peel strength$^2$+b−c, wherein c may be a value that satisfies a×peel strength$^2$+b>c>0.

In one form of the first method of producing a secondary battery disclosed here, charging rate={a×peel strength$^2$+b}×c', wherein c' may be a value that satisfies 0<c'<1.

A second method of producing a secondary battery disclosed here includes forming a positive electrode active material layer containing a lithium- and manganese-containing composite oxide on a positive electrode current collector to produce a positive electrode; measuring a peel strength between the positive electrode active material layer and the positive electrode current collector; producing a secondary battery assembly including the positive electrode, a negative electrode, and a nonaqueous electrolyte using the positive electrode; and performing initial charging while restraining the secondary battery assembly, wherein, when the secondary battery assembly is initially charged, a restraining pressure is determined based on the measured peel strength, and in a predetermined peel strength range, a higher restraining pressure is set for a secondary battery assembly including a positive electrode having a low peel strength than for a secondary battery assembly including a positive electrode having a large peel strength.

In such a configuration, in the lithium ion secondary battery including a positive electrode having a low peel strength between the positive electrode active material layer and the positive electrode current collector, when the restraining pressure is changed, it is possible to prevent the lithium- and manganese-containing composite oxide which is a positive electrode active material from being exposed to an acid (particularly, HF) generated during initial charging without increasing the valence of manganese. Accordingly, it is possible to prevent low-valence manganese from being eluted from the lithium- and manganese-containing composite oxide. Thus, it is also possible to produce the secondary battery using a positive electrode having a low peel strength between the positive electrode active material layer and the positive electrode current collector which was discarded in the related art. Therefore, it is possible to reduce the number of positive electrodes to be discarded and as a result, it is possible to produce the secondary battery with a high yield.

In one form of the second method of producing a secondary battery disclosed here, in the process of initial charging, ultrasonic waves may be emitted toward an interface between the positive electrode active material layer and the positive electrode current collector, and the restraining pressure may be changed according to a transmission intensity of the ultrasonic waves.

In such a configuration, it is possible to further optimize the restraining pressure in the initial charging process.

In one form of the second method of producing a secondary battery disclosed here, when a transmission intensity of ultrasonic waves is equal to or less than a predetermined value, the restraining pressure may be increased.

In one form of the second method of producing a secondary battery disclosed here, restraining pressure≥d×peel strength+e, wherein d<0, e>0.

In one form of the second method of producing a secondary battery disclosed here, restraining pressure=d×peel strength+e+f, wherein f>0.

In one form of the second method of producing a secondary battery disclosed here, restraining pressure={d×peel strength+e}×f', wherein f'>1.

BRIEF DESCRIPTION OF THE DRAWINGS

Features, advantages, and technical and industrial significance of exemplary embodiments of the disclosure will be described below with reference to the accompanying drawings, in which like numerals denote like elements, and wherein.

DETAILED DESCRIPTION OF EMBODIMENTS

Embodiments of the present disclosure will be described below with reference to the drawings. Here, components other than those particularly mentioned in this specification that are necessary for implementation of the present disclosure (for example, a general configuration and a producing process of a secondary battery that do not characterize the present disclosure) can be recognized by those skilled in the art as design matters based on the related art in the field. The present disclosure can be implemented based on content disclosed in this specification and common technical knowledge in the field. In addition, the sizes (a length, a width, a thickness, and the like) in the drawings do not reflect actual sizes.

Here, the term "secondary battery" in this specification refers to a general power storage device capable of repeatedly performing charging and discharging, and is a term that includes a so-called storage battery such as a lithium ion secondary battery and a power storage element such as an electric double-layer capacitor. The present disclosure will be described below in detail with reference to embodiments, but the following embodiments are not intended to limit the present disclosure.

First Embodiment

Figure 1:
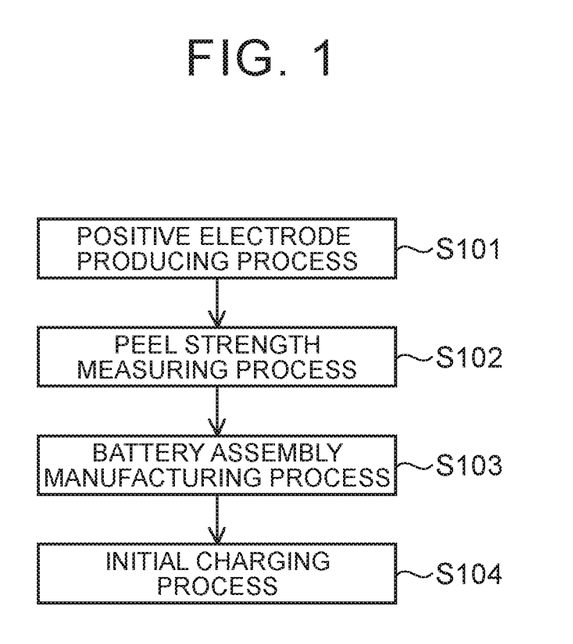
FIG. 1 is a flowchart showing processes of a method of producing a secondary battery according to a first embodiment of the present disclosure.

FIG. 1 shows processes of a method of producing a secondary battery according to a first embodiment. The method of producing a secondary battery according to the first embodiment shown in FIG. 1 includes a process (positive electrode producing process) S101 in which a positive electrode active material layer containing a lithium- and manganese-containing composite oxide is formed on a positive electrode current collector to produce a positive electrode, a process (peel strength measuring process) S102 in which a peel strength between the positive electrode active material layer and the positive electrode current collector is measured, a process (battery assembly manufacturing process) S103 in which a secondary battery assembly including the positive electrode, a negative electrode, and a nonaqueous electrolyte is produced using the positive electrode, and a process (initial charging process) S104 in which the secondary battery assembly is initially charged. In the initial charging process S104, a charging rate is determined based on the measured peel strength, and in a predetermined peel strength range, a lower charging rate is set for a secondary battery assembly including a positive electrode having a low peel strength than for a secondary battery assembly including a positive electrode having a large peel strength.

Figure 2:
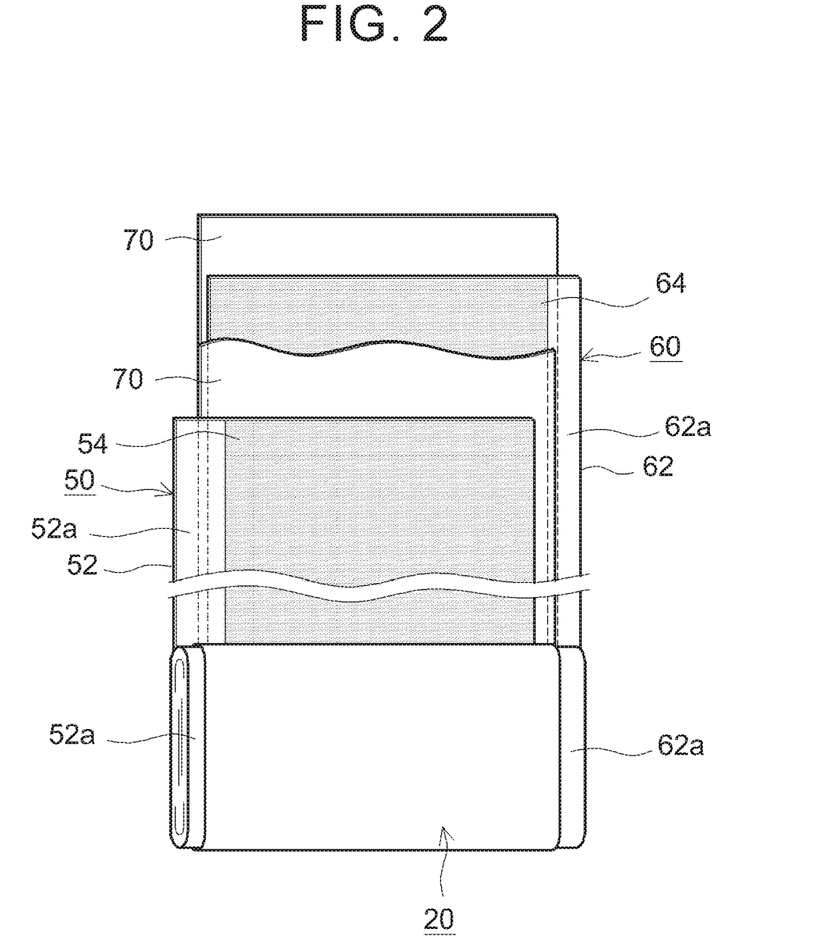
FIG. 2 is a schematic diagram showing a configuration of a wound electrode body of a lithium ion secondary battery obtained by a method of producing a secondary battery according to first and second embodiments of the present disclosure.
Figure 3:
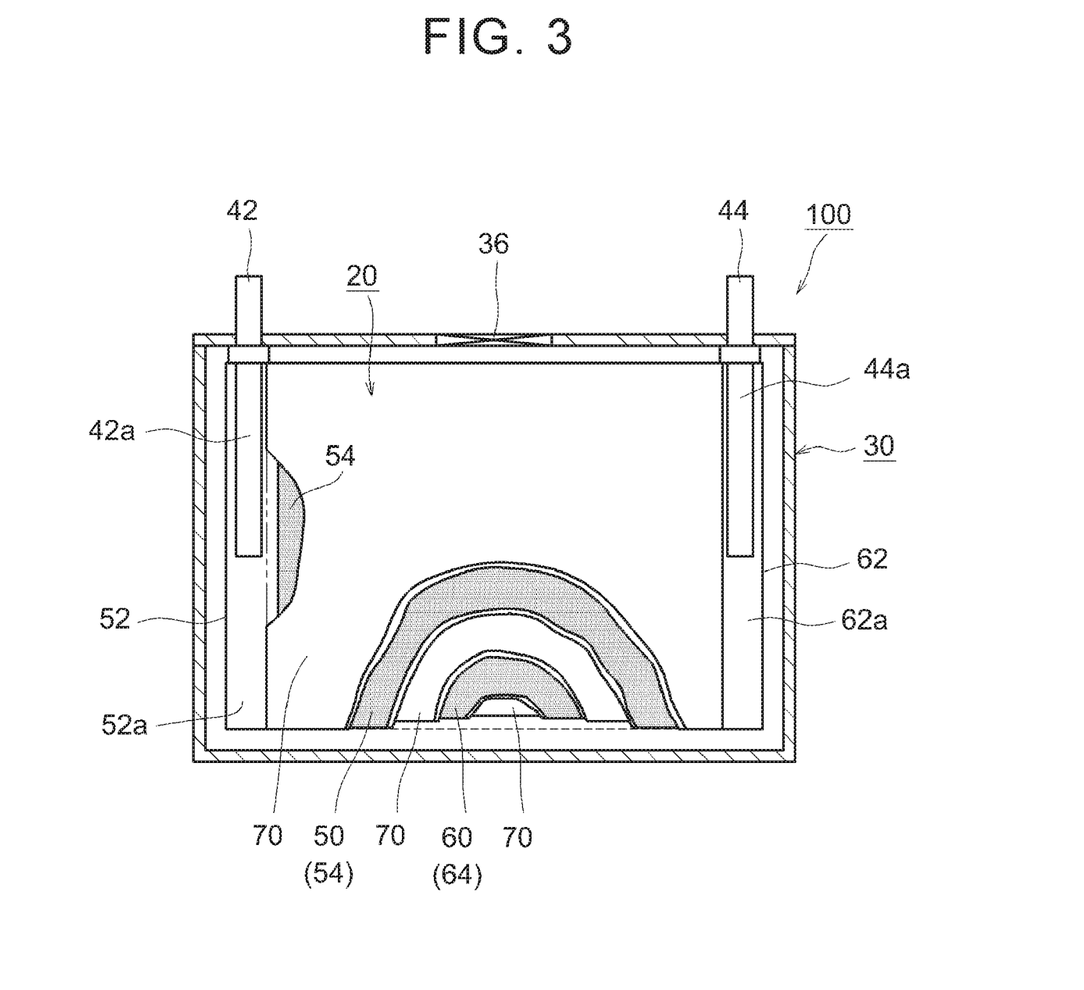
FIG. 3 is a sectional view schematically showing an internal structure of a lithium ion secondary battery obtained by the method of producing a secondary battery according to the first and second embodiments of the present disclosure.

FIG. 2 is a diagram schematically showing a configuration of a wound electrode body 20 of a lithium ion secondary battery 100 which is an example of a secondary battery obtained by the production method according to the present embodiment. FIG. 3 is a diagram schematically showing an internal structure of the lithium ion secondary battery 100 which is an example of a secondary battery obtained by the production method according to the present embodiment.

First, the positive electrode producing process S101 will be described. In the positive electrode producing process S101, a positive electrode active material layer 54 containing a lithium- and manganese-containing composite oxide is formed on a positive electrode current collector 52 to produce a positive electrode 50. The process S101 can be performed by, for example, applying a composition for forming a positive electrode active material layer, which contains a lithium- and manganese-containing composite oxide, to the positive electrode current collector 52 and performing drying, and performing pressing as necessary.

A type of the lithium- and manganese-containing composite oxide is not particularly limited as long as it can function as a positive electrode active material. For example, a composite oxide represented by $Li_mMn_xM_yO_n$ (where m, x, y, and n satisfy $0.96 \leq m \leq 1.20$, $1.0 \leq x \leq 2.0$, $0 < y \leq 1.0$, $2 \leq n \leq 4$, and $x > y$, and M is at least one selected from the group consisting of Ni, Co, Ti, Fe, W, Cr, V, and Cu) as an average composition can be used. The form of the lithium- and manganese-containing composite oxide is not particularly limited, but lithium- and manganese-containing composite oxide particles are typically used. When the lithium- and manganese-containing composite oxide particles are used, an average particle size is generally 20 μm or less (typically 1 to 20 μm, for example, 5 to 15 μm). Here, the "average particle size" in this specification refers to a particle size ($D_{50}$, also referred to as a median diameter) corresponding to a cumulative frequency of 50 volume % from the side of fine particles having a small particle size in a volume-based particle size distribution based on a general laser diffraction and light scattering method. As the positive electrode active material, a compound other than the lithium- and manganese-containing composite oxide may be contained in the composition for forming a positive electrode active material layer. As the compound, a compound known as a positive electrode active material of a lithium ion secondary battery may be used. The positive electrode active material is contained preferably at greater than 50 mass %, more preferably 80 mass % to 97 mass %, and most preferably 85 mass % to 96 mass % with respect to the total solid content of the composition for forming a positive electrode active material layer.

The composition for forming a positive electrode active material layer typically contains a conductive material, a binder, and a solvent. As an example of the conductive material, a carbon material such as carbon black (for example, acetylene black, furnace black, and Ketchen black), coke, graphite (for example, natural graphite, and modified materials thereof, and artificial graphite) may be exemplified. Among these, carbon black is preferable. The conductive material is contained at preferably 0.1 to 20 mass %, and more preferably 1 to 15 mass % with respect to the positive electrode active material. As an example of the binder, polyvinylidene fluoride (PVdF), polyacrylate, polymethacrylate, and the like may be exemplified. The binder is contained at preferably 0.5 to 10 mass % and more preferably 1 to 8 mass % with respect to the positive electrode active material. As an example of the solvent, water, N-methyl-2-pyrrolidone (NMP), methyl ethyl ketone, toluene, and the like may be exemplified.

The composition for forming a positive electrode active material layer may contain a component other than the positive electrode active material, the conductive material, the binder, and the solvent. As an example of the component, a thickener and the like may be exemplified. As an example of the thickener, a cellulosic polymer such as carboxymethyl cellulose (CMC), methylcellulose, and hydroxypropylcellulose may be exemplified. Among these, carboxymethyl cellulose is preferable. The thickener is contained at preferably 0.5 to 10 mass % and more preferably 1 to 8 mass % with respect to the positive electrode active material.

The form of the composition for forming a positive electrode active material layer is not particularly limited as long as it can be applied to the positive electrode current collector 52. A composition in the form of a paste, a slurry, an ink, a granulated substance or the like may be used.

The composition for forming a positive electrode active material layer can be prepared by mixing the lithium- and manganese-containing composite oxide, the conductive material, the binder, and the solvent, and other components as necessary using a known mixing device. As the mixing device, a planetary mixer, a homogenizer, a Clearmix, a Filmix, a bead mill, a ball mill, a kneading extruder, and the like may be exemplified.

As the positive electrode current collector 52, a foil-like body made of a metal having favorable conductivity (for example, aluminum, nickel, titanium, and stainless steel) can be appropriately used, and more appropriately, an aluminum foil is used.

The composition for forming a positive electrode active material layer is applied to the positive electrode current collector according to a known method. For example, a coating device such as a slit coater, a die coater, a comma coater, a gravure coater, or a dip coater can be used to apply the composition for forming a positive electrode active material layer to the positive electrode current collector 52. Here, the positive electrode active material layer 54 may be formed only on one surface of the positive electrode current collector 52 or may be formed on both surfaces thereof, and preferably, formed on both surfaces thereof. Thus, the composition for forming a positive electrode active material layer is applied to one surface or both surfaces of the positive electrode current collector 52, and preferably applied to both surfaces thereof.

After the application, drying is performed. Drying can be performed by removing the solvent using a drying device such as a drying furnace. A drying temperature and a drying time may be appropriately determined according to a type and amount of the solvent included in the applied composition for forming a positive electrode active material layer.

After the drying, pressing may be performed in order to adjust the thickness, the density, and the like of the positive electrode active material layer 54. Next, when the positive electrode current collector 52 on which the positive electrode active material layer 54 is formed is processed to a predetermined size, it is possible to obtain the positive electrode (positive electrode sheet) 50 in which the positive electrode active material layer 54 is formed on the positive electrode current collector 52.

Next, the peel strength measuring process S102 will be described. In the peel strength measuring process S102, a peel strength between the positive electrode active material layer 54 and the positive electrode current collector 52 is measured. When the peel strength is measured, a known peel strength measurement method can be used. As an example of the peel strength measurement method, a method in which a 90° peeling test is performed according to JISZ0237: 2009 (test method for adhesive tapes and adhesive sheets) may be exemplified. As a test piece provided to measure the peel strength, a cut out surplus piece generated when processing into a predetermined size is performed in the positive electrode producing process S101 may be used. Alternatively, in the positive electrode producing process S101, a size of a test piece is added to a size of a desired positive electrode, a positive electrode current collector in which a positive electrode active material layer is formed is produced, and the positive electrode and the test piece may be produced during size processing. It is more appropriate to produce a long positive electrode sheet roll that is great in length and collect test pieces before and after or during a process of performing cutting into a positive electrode sheet 50 having a size corresponding to one sheet than to prepare a plurality of positive electrode sheets 50.

On the other hand, the battery assembly manufacturing process S103 is performed. In the battery assembly manufacturing process S103, a secondary battery assembly including the positive electrode 50 obtained in the positive electrode producing process S101, a negative electrode 60, and a nonaqueous electrolyte (not shown) is produced. Here, the order of performing the peel strength measuring process S102 and the battery assembly manufacturing process S103 is not particularly limited. Either the peel strength measuring process S102 or the battery assembly manufacturing process S103 may be performed first and both may be performed at the same time.

The battery assembly manufacturing process S103 can be performed according to a general method. For example, the negative electrode 60, and a separator 70 are prepared, and the positive electrode 50 obtained in the positive electrode producing process S101 is used to produce the electrode body 20 shown in FIG. 2. Here, while a wound electrode body is produced as the electrode body 20 in the present embodiment, the form of the electrode body 20 is not limited thereto, and the electrode body 20 may be produced as a laminated electrode body according to a known method.

The negative electrode 60 has typically a configuration in which a negative electrode active material layer 64 is provided on one surface or both surfaces (appropriately both surfaces) of a negative electrode current collector 62. The negative electrode 60 can be produced by applying a composition for forming a negative electrode active material layer, which contains a negative electrode active material, a thickener, a binder, and a solvent, to the negative electrode current collector 62, and performing drying, and performing pressing as necessary. As the negative electrode active material, for example, a carbon material such as graphite, hard carbon, and soft carbon may be used. As the binder, for example, styrene butadiene rubber (SBR) may be used. As the thickener, for example, carboxymethyl cellulose (CMC) may be used. As the solvent, water and the like may be used. As the negative electrode current collector 62, a foil-like body made of a metal having favorable conductivity (for example, copper, nickel, titanium, and stainless steel) can be appropriately used, and more appropriately, a copper foil is used. Application of the composition for forming a negative electrode active material layer to the negative electrode current collector 62, drying, and any pressing operation can be performed according to a known method.

As the separator 70, for example, a porous sheet (film) made of a polyethylene (PE), polypropylene (PP), polyester, cellulose, or polyamide resin may be exemplified. Such a porous sheet may have a single layer structure or a laminated structure having two or more layers (for example, a three-layer structure in which a PP layer is laminated on both surfaces of a PE layer). A heat resistant layer (HRL) may be provided on a surface of the separator 70.

The wound electrode body 20 can be produced using the positive electrode sheet 50, the negative electrode sheet 60, and the separator 70 according to a known method. For example, the wound electrode body 20 can be produced by winding a laminate in which the positive electrode sheet 50 and the negative electrode sheet 60 are laminated with two separators 70 therebetween in a longitudinal direction, and performing pressing and squeezing in a lateral direction. In this case, as shown in FIG. 2, typically, a positive electrode active material layer non-forming portion 52a provided at an end of the positive electrode sheet 50 in a width direction and a negative electrode active material layer non-forming portion 62a provided at an end of the negative electrode sheet 60 in a width direction are laminated to protrude in directions opposite to each other and are wound. Accordingly, when the positive electrode active material layer non-forming portion 52a and the negative electrode active material layer non-forming portion 62a are integrated for power collection, it is possible to form the electrode body 20 having favorable current collection efficiency. Here, the electrode body 20 may be produced by winding the laminate itself so that the wound cross section becomes flattened.

Next, as shown in FIG. 3, the wound electrode body 20 is accommodated in a battery case 30 according to a known method. Specifically, a main body of the battery case 30, which has an opening, and a lid of the battery case 30, which has an inlet for a nonaqueous electrolyte solution, are prepared. The lid has a size which closes the opening of the main body of the battery case 30. In addition, a thin-walled safety valve 36 with a configuration set such that, when an internal pressure of the battery case 30 increases to a predetermined level or higher, the internal pressure is released, and an inlet (not shown) for injecting a nonaqueous electrolyte solution are provided in the lid. For the battery case 30, for example, a lightweight metal material having favorable thermal conductivity such as aluminum is used.

Next, a positive electrode terminal 42 and a positive electrode current collecting plate 42a, and a negative electrode terminal 44 and a negative electrode current collecting plate 44a are attached to the lid of the battery case 30. The positive electrode current collecting plate 42a and the negative electrode current collecting plate 44a are welded to the positive electrode current collector 52 and the negative electrode current collector 62 exposed to ends of the wound electrode body 20, respectively, by ultrasonic welding or the like. Then, the wound electrode body 20 is accommodated in the battery case 30 from the opening of the main body of the battery case 30, and the main body and the lid of the battery case 30 are welded by laser welding or the like.

Next, a nonaqueous electrolyte solution (not shown) is injected from the inlet of the lid of the battery case 30. After the nonaqueous electrolyte solution is injected, the inlet is sealed, and thus it is possible to obtain a lithium ion secondary battery assembly shown in FIG. 3. The same nonaqueous electrolyte solution as in a lithium ion secondary battery of the related art can be used. Typically, a nonaqueous electrolyte solution in which a supporting salt is included in an organic solvent (nonaqueous solvent) can be used. As the nonaqueous solvent, an organic solvent such as various carbonates, ethers, esters, nitriles, sulfones, and lactones which are used in an electrolyte solution of a general lithium ion secondary battery can be used without particular limitation. As a specific example, ethylene carbonate (EC), propylene carbonate (PC), diethyl carbonate (DEC), dimethyl carbonate (DMC), ethyl methyl carbonate (EMC), monofluoroethylene carbonate (MFEC), difluoroethylene carbonate (DFEC), monofluoromethyl difluoromethyl carbonate (FDMC), trifluorodimethyl carbonate (TFDMC), and the like may be exemplified. Such nonaqueous solvents can be used alone or in appropriate combination of two or more thereof. As the supporting salt, for example, a lithium salt such as $LiPF_6$, $LiBF_4$, and $LiClO_4$ (preferably $LiPF_6$) can be appropriately used. A concentration of the supporting salt is preferably 0.7 mol/L or more and 1.3 mol/L or less. Here, the nonaqueous electrolyte solution may contain various additives, for example, a gas generating agent, a film forming agent, a dispersant, and a thickener.

Next, the initial charging process S104 will be described. In the initial charging process S104, the secondary battery assembly is initially charged. In the initial charging process S104, a charging rate is determined based on the peel strength measured in the peel strength measuring process S102, and in a predetermined peel strength range, a lower charging rate is set for a secondary battery assembly including a positive electrode having a low peel strength than for a secondary battery assembly including a positive electrode having a large peel strength.

A specific example of determining a charging rate will be described with reference to Test Example 1. A battery of Test Example 1 was produced according to the following method. $LiNi_{0.5}Mn_{1.5}O_4$ having an average particle size of 10 μm as a lithium- and manganese-containing oxide, acetylene black (AB) as a conductive material, and polyvinylidene fluoride (PVDF) as a binder (mass ratio of $LiNi_{0.5}Mn_{1.5}O_4$:AB:PVDF=87:10:3) were mixed with N-methyl pyrrolidone (NMP) to prepare a slurry for forming a positive electrode active material layer. The slurry was applied to both surfaces of an aluminum foil (positive electrode current collector) and dried, and then processing to a predetermined size was performed to produce a positive electrode sheet. In this case, when a mixing time during slurry preparation was adjusted in order to simulate variations in peel strength during production, various positive electrode sheets having different peel strengths between the positive electrode active material layer and the positive electrode current collector were produced. In addition, when the positive electrode sheet was produced, a test piece for measuring a peel strength was also produced. In addition, a natural graphite-based carbon material (C) having an average particle size of 20 μm as a negative electrode active material, styrene butadiene rubber (SBR) as a binder, and carboxymethyl cellulose (CMC) as a thickener (mass ratio of C:SBR:CMC=98:1:1) were mixed with deionized water to prepare a slurry for forming a negative electrode active material layer. The slurry was applied to both surfaces of a copper foil and dried, and then processing to a predetermined size was performed to produce a negative electrode sheet. In addition, a separator sheet (porous polyolefin sheet) was prepared. The produced positive electrode sheet and negative electrode sheet, and two separator sheets were laminated and wound to produce an electrode body. The produced electrode body to which a current collector was attached was accommodated in a rectangular battery case together with a nonaqueous electrolyte solution to obtain a lithium ion secondary battery assembly. As the nonaqueous electrolyte solution, a solution in which $LiPF_6$ with a concentration of 1 mol/L was dissolved in a solvent mixture containing monofluoroethylene carbonate (MFEC) and monofluoromethyl difluoromethyl carbonate (FDMC) (volume ratio 50:50) was used. The lithium ion secondary battery assembly was restrained, a restraining pressure of 15 kg/cm$^2$ was applied to an electrode area, and initial charging was performed at various charging rates. Then, discharging was performed from a full charged state, and a discharge capacity (initial capacity) was obtained. Thus, the lithium ion secondary battery of Test Example 1 was obtained. The lithium ion secondary battery of Test Example 1 on which initial charging was performed was left in an environment at 60° C., and charging was performed at a constant current of 2C up to 4.9 V and discharging was performed at a constant current of 2C up to 3.5 V. This charging and discharging was set as one cycle, which was performed over a total of 200 cycles. Then, a battery capacity after charging and discharging over 200 cycles was obtained (battery capacity after charging and discharging over 200 cycles/initial capacity) and multiplied by 100 to obtain a capacity retention rate (%). On the other hand, a peel strength between the positive electrode active material layer and the positive electrode current collector of the positive electrode sheet used to produce the lithium ion secondary battery was measured using a 90° peeling test according to JISZ0237: 2009 (test method for adhesive tapes and adhesive sheets). Specifically, using a 90° peel testing machine ("SV-201-NA-50SL" commercially available from IMADA SEISAKUSHO Co., Ltd.), the positive electrode active material layer was fixed to a test stand, the positive electrode current collector was pulled in a direction of 90°, and a peel strength was measured. The test was performed a plurality of times. The most frequent value was used as a peel strength between the positive electrode active material layer and the positive electrode current collector of the positive electrode sheet. A peel strength of another positive electrode sheet was obtained as a relative value when a peel strength of a positive electrode sheet obtained when mixing during slurry preparation was performed under standard conditions was set as 100.

Figure 4:
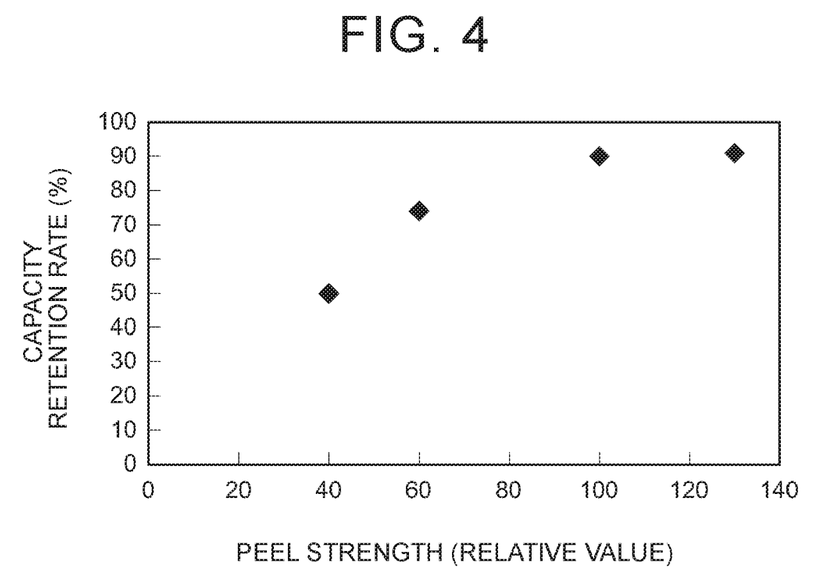
FIG. 4 is a graph showing the relationship between a peel strength and a capacity retention rate of a lithium ion secondary battery of Test Example 1.

FIG. 4 is a graph showing the relationship between a peel strength and a capacity retention rate of the lithium ion secondary battery of Test Example 1 on which, as initial charging, charging was performed at a constant current of 0.2C (a current value of ⅕ C of a capacity estimated from an amount of the positive electrode active material) up to 4.9 V, and constant voltage charging was then performed until the current value reached 1/50 C. As described above, when the peel strength is lower than a certain value, the capacity retention rate tends to decrease as the peel strength decreases. In Test Example 1, when a cross section of the positive electrode sheet having a low peel strength and a cross section of the positive electrode sheet having a large peel strength were observed under an electronic microscope, it was found that the positive electrode sheet having a low peel strength had relatively many portions in which the positive electrode active material layer and the positive electrode current collector were not in close contact with each other. In addition, in those portions, it was confirmed that a metal was eluted from $LiNi_{0.5}Mn_{1.5}O_4$, and it was suggested that manganese was eluted from $LiNi_{0.5}Mn_{1.5}O_4$. Based on the above result, the reason for the above trend is inferred to be as follows. The positive electrode sheet having a low peel strength between the positive electrode active material layer and the positive electrode current collector had relatively many portions in which the positive electrode active material layer and the positive electrode current collector were not in close contact each other. In those portions, no electrons were supplied from the positive electrode current collector, and the valence of manganese did not increase during initial charging, and exposure to an acid (particularly, HF) generated during initial charging occurred. Thus, manganese having a low valence was likely to be eluted from the lithium- and manganese-containing composite oxide.

Figure 5:
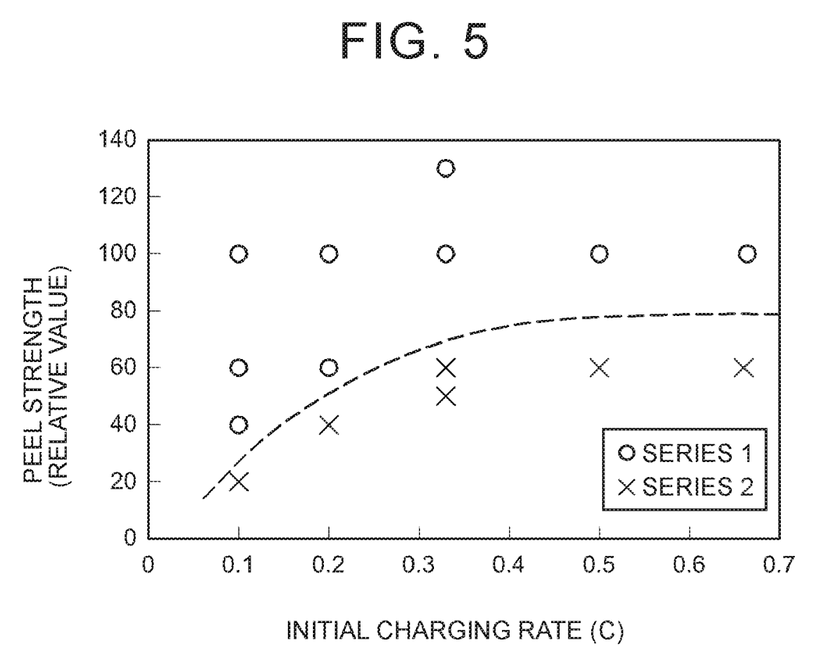
FIG. 5 is a graph showing correlations of a capacity retention rate with a peel strength and a charging rate during initial charging of the lithium ion secondary battery of Test Example 1.

FIG. 5 is a graph showing correlations of a capacity retention rate with a peel strength and a charging rate during initial charging. In FIG. 5, a test lithium ion secondary battery having a capacity retention rate that is equal to or greater than an acceptance value (accepted product) is plotted as a series 1 (o in the graph), and a test lithium ion secondary battery having a capacity retention rate that is less than an acceptance value (rejected product) is plotted as a series 2 (x in the graph). As shown in FIG. 5, it can be seen that, as peel strength decreases, when the charging rate is reduced, the number of accepted lithium ion secondary batteries increases. The reason for this is inferred to be as follows. In a lithium ion secondary battery assembly including a positive electrode having a low peel strength, when the charging rate is reduced, a lithium- and manganese-containing composite oxide serving as a positive electrode active material is prevented from being exposed to an acid (particularly, HF) generated during initial charging without increasing the valence of manganese. Therefore, it is possible to prevent low-valence manganese from being eluted from the lithium- and manganese-containing composite oxide.

The dashed line in FIG. 5 represents an acceptance line of the peel strength and the charging rate of the lithium ion secondary battery. The dashed line in FIG. 5 can be approximated by charging rate=a×(peel strength)$^2$+b(a>0, b≈0).

Here, based on the findings obtained from Test Example 1, for example, the charging rate in the initial charging process S104 is determined to satisfy charging rate≤a×(peel strength)$^2$+b, (preferably, charging rate<a×(peel strength)$^2$+b). For example, a formula in which the charging rate is slightly lower than that of the approximate formula of the acceptance line: charging rate=a×(peel strength)$^2$+b−c (c is a value that satisfies a×(peel strength)$^2$+b>c>0, for example, 0.05 to 0.15), or charging rate={a×(peel strength)$^2$+b}×c' (c' is a value that satisfies 0<c'<1, for example, 0.75 to 0.90) is determined, a peel strength is substituted into the formula, and thus the charging rate can be determined. According to such a method, in a predetermined peel strength range (particularly, in a range in which a peel strength is equal to or less than a predetermined value), a lower charging rate is set for a lithium ion secondary battery assembly including a positive electrode having a low peel strength than for a lithium ion secondary battery assembly including a positive electrode having a large peel strength.

Alternatively, based on the results in FIG. 5, a charging rate of a specific value may be assigned for a specific range of a peel strength such that initial charging is performed at a charging rate of 0.5C when a peel strength is 80 or more, a charging rate of 0.2C when a peel strength is 60 or more and less than 80, and a charging rate of 0.1C when a peel strength is 40 or more and less than 60, and the charging rate may be determined. In such a method also, in a predetermined peel strength range (particularly, in a range in which a peel strength is equal to or less than a predetermined value), a lower charging rate is set for a lithium ion secondary battery assembly including a positive electrode having a low peel strength than for a lithium ion secondary battery assembly including a positive electrode having a large peel strength.

As described above, in the initial charging process S104, based on the test results of the peel strength and the charging rate, it is possible to determine a charging rate at which an accepted secondary battery can be provided for the positive electrode 50 having a specific peel strength. Specifically, when the relationship between the charging rate and the peel strength is formulated, the peel strength measured in the peel strength measuring process S102 is substituted into the formula, and thus the charging rate can be determined. In addition, based on the test results of the peel strength and the charging rate, a charging rate of a specific value is assigned for a specific range of a peel strength. Based on the assignment, the charging rate can be determined from the peel strength measured in the peel strength measuring process S102. Here, a method of determining a charging rate is not limited to the above method. Any method in which, in a predetermined peel strength range, a lower charging rate is set for a lithium ion secondary battery assembly including a positive electrode having a low peel strength than for a lithium ion secondary battery assembly including a positive electrode having a large peel strength may be used. Here, a positive electrode of which the peel strength measured in the peel strength measuring process S102 is too low may be discarded.

Initial charging can be performed such that, for example, an external power supply is connected between the positive electrode terminal 42 and the negative electrode terminal 44 of the produced lithium ion secondary battery assembly, and charging (typically, constant current charging) is performed at the determined charging rate up to a predetermined voltage. For the initial charging, constant current charging may be performed at the determined charging rate up to a predetermined voltage, and constant voltage charging may be then performed up to another predetermined voltage. In the initial charging process S104, it is preferable that the secondary battery assembly be restrained and initial charging be performed while applying a restraining pressure.

Here, in the peel strength measuring process S102, the peel strength is measured using a test piece separate from the positive electrode 50. Thus, it is not possible to accurately measure the peel strength between the positive electrode active material layer 54 and the positive electrode current collector 52 of the positive electrode 50 in some cases. In addition, after the peel strength measuring process S102, the peel strength between the positive electrode active material layer 54 and the positive electrode current collector 52 may be reduced due to impact or the like. In addition, in the initial charging process S104, the peel strength between the positive electrode active material layer 54 and the positive electrode current collector 52 may be lower than the measurement value in the peel strength measuring process S102. In addition, during charging, the peel strength between the positive electrode active material layer 54 and the positive electrode current collector 52 may change. Therefore, in the initial charging process S104, ultrasonic waves may be emitted toward an interface between the positive electrode active material layer 54 and the positive electrode current collector 52, and the charging rate may be changed according to a transmission intensity of the ultrasonic waves.

Figure 6:
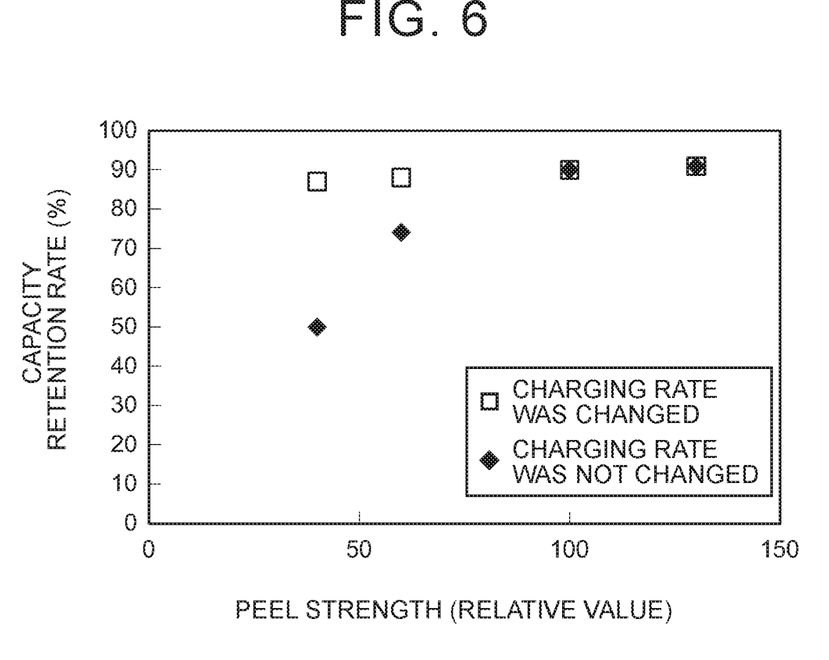
FIG. 6 is a graph showing results obtained when a charging and discharging rate of an assembly of the lithium ion secondary battery of Test Example 1 is changed according to a transmission intensity of ultrasonic waves and when the charging and discharging rate is not changed.

When ultrasonic waves are emitted toward the interface between the positive electrode active material layer 54 and the positive electrode current collector 52, attenuation occurs when ultrasonic waves are transmitted. An amount of attenuation is larger in a portion in which the positive electrode active material layer 54 and the positive electrode current collector 52 are not in close contact with each other than in a portion in which the positive electrode active material layer 54 and the positive electrode current collector 52 are in close contact with each other. Here, for example, when the transmission intensity of ultrasonic waves is equal to or less than a predetermined value, the charging rate is reduced. The inventors compared two cases in which constant current charging at 0.2C was performed for the lithium ion secondary battery assembly of Test Example 1 while scanning with an ultrasonic probe, and when an area of a portion in which the transmission intensity was 66% or less was greater than ⅕ of the total electrode area, the charging rate was lowered to 0.1C and the charging rate was not changed. The results are shown in FIG. 6. As shown in FIG. 6, if the charging rate is reduced when the transmission intensity of ultrasonic waves is equal to or less than a predetermined value, it is possible to obtain a lithium ion secondary battery having a high capacity retention rate even when a positive electrodes having a peel strength relative value of 60 and 40 (that is, the peel strength is low) is used. Therefore, in this manner, it is possible to further optimize the charging rate in the initial charging process S104.

Emission of ultrasonic waves and measurement of the transmission intensity can be performed according to known methods. For example, using a known ultrasonic inspection device (for example, refer to Japanese Unexamined Patent Application Publication No. 2015-215279 (JP 2015-215279 A)) used for examination of a laminate seal, the battery case 30 is provided between a transmitter and a receiver of the ultrasonic inspection device, and ultrasonic waves can be emitted in a direction perpendicular to a lamination direction of the positive electrode 50 and the negative electrode 60.

After the initial charging process S104, an aging process may be performed according to a known method. As described above, the lithium ion secondary battery 100 can be obtained. According to the production method of the present embodiment, when the charging rate is selected according to the peel strength between the positive electrode active material layer 54 and the positive electrode current collector 52, it is also possible to produce the lithium ion secondary battery 100 including the positive electrode 50 having a low peel strength between the positive electrode active material layer 54 and the positive electrode current collector 52 which was discarded in the related art. Therefore, it is possible to reduce the number of positive electrodes 50 to be discarded and as a result, it is possible to produce the lithium ion secondary battery 100 with a high yield.

Second Embodiment

Figure 7:
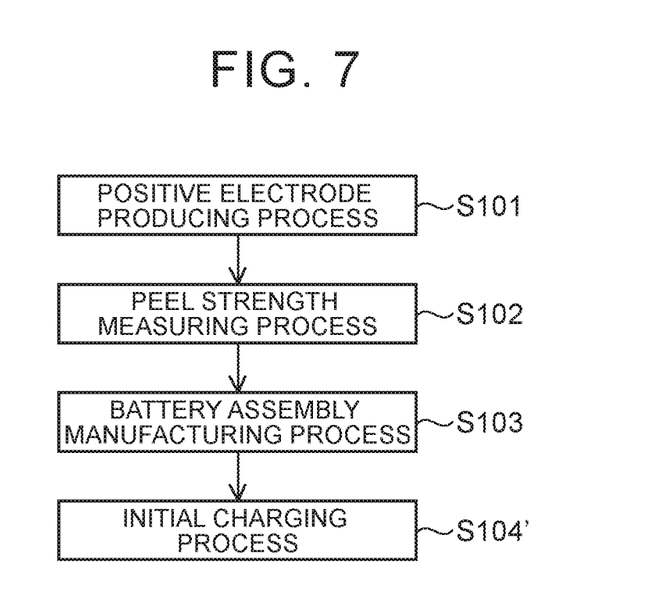
FIG. 7 is a flowchart showing processes of a method of producing a secondary battery according to the second embodiment of the present disclosure.

FIG. 7 shows processes of a method of producing a secondary battery according to a second embodiment. The method of producing a secondary battery according to the second embodiment shown in FIG. 7 includes a the process (positive electrode producing process) S101 in which a positive electrode active material layer containing a lithium- and manganese-containing composite oxide is formed on a positive electrode current collector to produce a positive electrode, a process (peel strength measuring process) S102 in which a peel strength between the positive electrode active material layer and the positive electrode current collector is measured, a process (battery assembly manufacturing process) S103 in which a secondary battery assembly including the positive electrode, a negative electrode, and a nonaqueous electrolyte is produced using the positive electrode, and a process (initial charging process) S104' in which initial charging is performed while restraining the secondary battery assembly. In the initial charging process S104', the restraining pressure is determined based on the measured peel strength, and in a predetermined peel strength range, a higher restraining pressure is set for a secondary battery assembly including a positive electrode having a low peel strength than for a secondary battery assembly including a positive electrode having a large peel strength.

Details of the positive electrode producing process S101, the peel strength measuring process S102, and the battery assembly manufacturing process S103 performed in the second embodiment are the same as those in the first embodiment, and descriptions thereof will be omitted.

The initial charging process S104' of the second embodiment will be described. In the initial charging process S104', initial charging is performed while restraining the secondary battery assembly. In the initial charging process S104', the restraining pressure is determined based on the peel strength measured in the peel strength measuring process S102, and in a predetermined peel strength range, a higher restraining pressure is set for a secondary battery assembly including a positive electrode having a low peel strength than for a secondary battery assembly including a positive electrode having a large peel strength.

A specific example of determining a charging rate will be described with reference to Test Example 2. A battery of Test Example 2 was produced according to the following method. First, according to the same method as in Test Example 1 described in the first embodiment, a lithium ion secondary battery assembly was produced using a positive electrode having various peel strengths between a positive electrode active material layer and a positive electrode current collector.

The lithium ion secondary battery assembly was restrained, various restraining pressures were applied to an electrode area, constant current charging was performed at a current value of 0.2C (⅕ C of a capacity estimated from an amount of a positive electrode active material) up to 4.9 V, and constant voltage charging was then performed until the current value reached 1/50 C. Then, discharging was performed up to 3.5 V and a discharge capacity (initial capacity) was obtained. Thus, the lithium ion secondary battery of Test Example 2 was obtained. The lithium ion secondary battery of Test Example 2 on which initial charging was performed was left in an environment at 60° C., and charging was performed at a constant current of 2C up to 4.9 V and discharging was performed at a constant current of 2C up to 3.5 V. This charging and discharging was set as one cycle, which was performed over a total of 200 cycles. Then, a battery capacity after charging and discharging over 200 cycles was obtained (battery capacity after charging and discharging over 200 cycles/initial capacity) and multiplied by 100 to obtain a capacity retention rate (%). On the other hand, a peel strength between the positive electrode active material layer and the positive electrode current collector of the positive electrode sheet was obtained according to the same method as in Test Example 1. A peel strength of another positive electrode sheet was obtained as a relative value when a peel strength of a positive electrode sheet obtained when mixing during slurry preparation was performed under standard conditions was set as 100.

Figure 8:
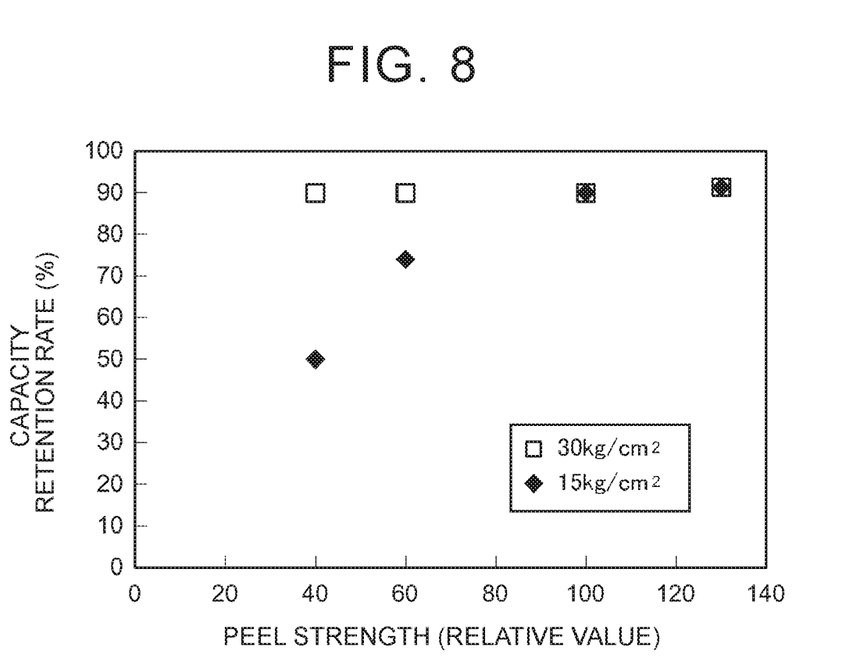
FIG. 8 is a graph showing the relationship between a peel strength and a capacity retention rate of a lithium ion battery with a restraining pressure during initial charging of 15 kg/cm$^2$ with respect to an electrode area and a lithium ion secondary battery with a restraining pressure of 30 kg/cm$^2$.

FIG. 8 is a graph showing the relationship between a peel strength and a capacity retention rate of the lithium ion battery on which a restraining pressure during initial charging was 15 kg/cm² with respect to an electrode area and the lithium ion secondary battery on which a restraining pressure during initial charging was 30 kg/cm². As shown in FIG. 8, it can be understood that, in the lithium ion secondary battery having a relative value of 60 and 40 (that is, the peel strength is low), the capacity retention rate is higher when the restraining pressure is increased. The reason for this is inferred to be as follows. When the restraining pressure is increased, in a positive electrode sheet having a low peel strength between a positive electrode active material layer and a positive electrode current collector, it is possible to reduce a portion in which the positive electrode active material layer and the positive electrode current collector are not in close contact with each other which is a portion in which no electrons are supplied from the positive electrode current collector. As a result, a lithium- and manganese-containing composite oxide serving as a positive electrode active material is prevented from being exposed to an acid (particularly, HF) generated during initial charging without increasing the valence of manganese. Therefore, it is possible to prevent low-valence manganese from being eluted from the lithium- and manganese-containing composite oxide.

Figure 9:
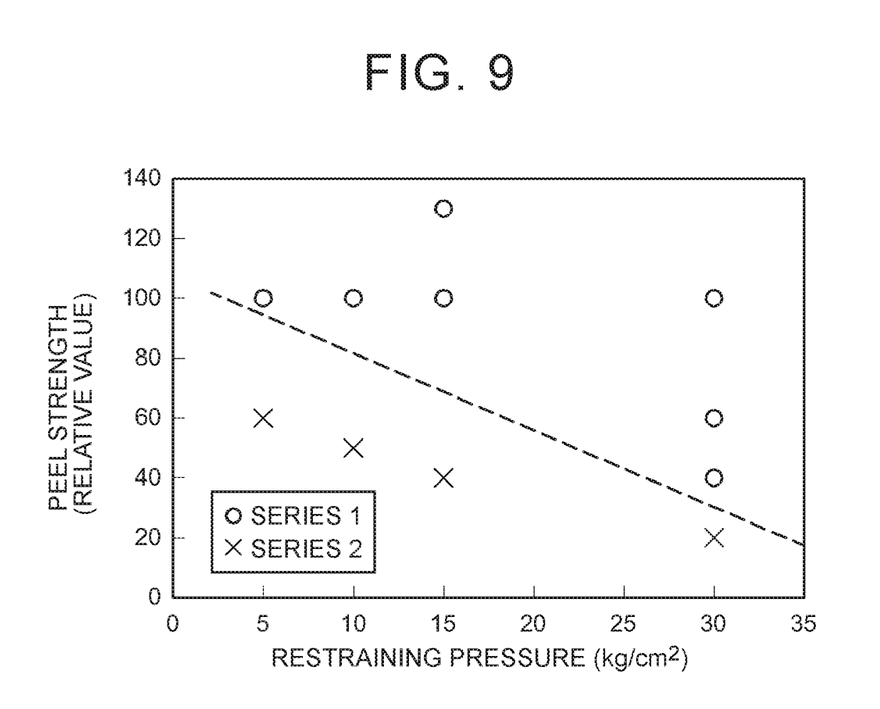
FIG. 9 is a graph showing a correlation between a peel strength and a restraining pressure, and a capacity retention of a lithium ion secondary battery of Test Example 2.

FIG. 9 is a graph showing correlations of a capacity retention rate with a peel strength and a restraining pressure. In FIG. 9, a test lithium ion secondary battery having a capacity retention rate that is equal to or greater than an acceptance value (here, 85%) (accepted product) is plotted as a series 1 (o in the graph), and a test lithium ion secondary battery having a capacity retention rate that is less than an acceptance value (rejected product) is plotted as a series 2 ((x in the graph). As shown in FIG. 9, it can be seen that, as the peel strength decreases, when the restraining pressure is higher, the number of accepted lithium ion secondary batteries increases.

The dashed line in FIG. 9 represents an acceptance line of the peel strength and the charging rate of the lithium ion secondary battery. The dashed line in FIG. 9 can be approximated by restraining pressure=d×(peel strength)+e (d<0, e>0).

Here, based on the findings obtained from Test Example 2, for example, the restraining pressure in the initial charging process S104' is determined to satisfy restraining pressure≥d×(peel strength)+e (preferably, restraining pressure>d×(peel strength)+e). For example, a formula in which the restraining pressure is slightly higher than that of the approximate formula of the acceptance line: restraining pressure=d×(peel strength)+e+f (f>0), or restraining pressure={d×(peel strength)+e}×f'(f'>1) is determined, a peel strength is substituted into the formula, and thus the restraining pressure can be determined. According to such a method, in a predetermined peel strength range (particularly, in a range in which a peel strength is equal to or less than a predetermined value), a higher restraining pressure is set for a lithium ion secondary battery assembly including a positive electrode having a low peel strength than for a lithium ion secondary battery assembly including a positive electrode having a large peel strength.

Alternatively, based on the results in FIG. 9, a restraining pressure of a specific value may be assigned for a specific range of a peel strength such that initial charging is performed at a restraining pressure of 15 kg/cm² when a peel strength is 80 or more, a restraining pressure of 22.5 kg/cm² when a peel strength is 60 or more and less than 80, and a restraining pressure of 30 kg/cm² when a peel strength is 40 or more and less than 60, and the restraining pressure may be determined. In such a method also, in a predetermined peel strength range (particularly, in a range in which a peel strength is equal to or less than a predetermined value), a higher restraining pressure is set for a lithium ion secondary battery assembly including a positive electrode having a low peel strength than for a lithium ion secondary battery assembly including a positive electrode having a large peel strength.

As described above, in the initial charging process S104', based on the test results of the peel strength and the restraining pressure, it is possible to determine a restraining pressure at which an accepted secondary battery can be provided for the positive electrode 50 having a specific peel strength. Specifically, when the relationship between the restraining pressure and the peel strength is formulated, the peel strength measured in the peel strength measuring process S102 is substituted into the formula, and thus the restraining pressure can be determined. In addition, based on the test results of the peel strength and the restraining pressure, a restraining pressure of a specific value is assigned for a specific range of a peel strength. Based on the assignment, the restraining pressure can be determined from the peel strength measured in the peel strength measuring process S102. Here, a method of determining a restraining pressure is not limited to the above method. Any method in which, in a predetermined peel strength range, a higher restraining pressure is set for a lithium ion secondary battery assembly including a positive electrode having a low peel strength than for a lithium ion secondary battery assembly including a positive electrode having a large peel strength may be used. Here, a positive electrode of which the peel strength measured in the peel strength measuring process S102 is too low may be discarded.

In the initial charging process S104', restraining can be performed according to a known method. For example, a known restraining tool or the like can be used for restraining. Initial charging can be performed such that, for example, an external power supply is connected between the positive electrode terminal 42 and the negative electrode terminal 44 of the produced lithium ion secondary battery assembly, and charging (typically, constant current charging) is performed to a predetermined voltage. For the initial charging, constant current charging may be performed at the determined charging rate up to a predetermined voltage, and constant voltage charging may be then performed up to another predetermined voltage.

Here, in the peel strength measuring process S102, the peel strength is measured using a test piece separate from the positive electrode 50. Thus, it is not possible to accurately measure the peel strength between the positive electrode active material layer 54 and the positive electrode current collector 52 of the positive electrode 50 in some cases. In addition, after the peel strength measuring process S102, the peel strength between the positive electrode active material layer 54 and the positive electrode current collector 52 may be reduced due to impact or the like. In addition, in the initial charging process S104', the peel strength between the positive electrode active material layer 54 and the positive electrode current collector 52 may be lower than the measurement value in the peel strength measuring process S102. In addition, during charging, the peel strength between the positive electrode active material layer 54 and the positive electrode current collector 52 may change. Therefore, the initial charging process S104', ultrasonic waves may be emitted toward an interface between the positive electrode active material layer and the positive electrode current collector, and the restraining pressure may be changed according to a transmission intensity of the ultrasonic waves.

When ultrasonic waves are emitted toward the interface between the positive electrode active material layer 54 and the positive electrode current collector 52, attenuation occurs when ultrasonic waves are transmitted. An amount of attenuation is larger in a portion in which the positive electrode active material layer 54 and the positive electrode current collector 52 are not in close contact with each other than in a portion in which the positive electrode active material layer 54 and the positive electrode current collector 52 are in close contact with each other. Here, for example, when the transmission intensity of ultrasonic waves is equal to or less than a predetermined value, the restraining pressure is increased. Therefore, in this manner, it is possible to further optimize the restraining pressure in the initial charging process S104'.

After the initial charging process S104', an aging process may be performed according to a known method. As described above, the lithium ion secondary battery 100 can be obtained. According to the production method of the present embodiment, when the restraining pressure is selected according to the peel strength between the positive electrode active material layer 54 and the positive electrode current collector 52, it is also possible to produce the lithium ion secondary battery 100 including the positive electrode 50 having a low peel strength between the positive electrode active material layer 54 and the positive electrode current collector 52 which was discarded in the related art. Therefore, it is possible to reduce the number of positive electrodes 50 to be discarded and as a result, it is possible to produce the lithium ion secondary battery 100 with a high yield.

Here, while the first embodiment and the second embodiment have been described as separate forms, the method of producing a secondary battery disclosed here can be performed in a combination of the first embodiment and the second embodiment. Specifically, both the charging rate and the restraining pressure may be changed according to the peel strength measured in the peel strength measuring process.

The lithium ion secondary battery 100 obtained as described above can be used for various applications. Appropriate applications may include a driving power supply mounted in a vehicle such as an electric vehicle (EV), a hybrid vehicle (HV), and a plug-in hybrid vehicle (PHV). Typically, the lithium ion secondary battery 100 may be used in the form of an assembled battery in which a plurality of batteries are connected in series and/or in parallel.

The rectangular lithium ion secondary battery 100 including a flat wound electrode body has been exemplified above. However, the method of producing a secondary battery disclosed here can be applied for production of other types of lithium ion secondary battery. For example, the method can be applied for production of a lithium ion secondary battery including a laminated electrode body. In addition, the method can be applied for production of a cylindrical lithium ion secondary battery, a laminated lithium ion secondary battery, and the like. In addition, the method can be applied for production of a nonaqueous electrolyte secondary battery other than a lithium ion secondary battery.

While specific examples of the present disclosure have been described above in detail, these are only examples, and do not limit the scope of the claims. The technologies described in the claims include various modifications and alternations of the specific examples exemplified above.

What is claimed is:

1. A method of producing a secondary battery comprising:
    forming a positive electrode active material layer containing a lithium- and manganese-containing composite oxide on a positive electrode current collector to produce a positive electrode;
    measuring a peel strength between the positive electrode active material layer and the positive electrode current collector;
    producing a secondary battery assembly including the positive electrode, a negative electrode, and a nonaqueous electrolyte using the positive electrode; and
    initially charging the secondary battery assembly,
    wherein, when the secondary battery assembly is initially charged, a charging rate is determined based on the measured peel strength, and in a predetermined peel strength range, the charging rate is set with the proviso that:
    when the measured peel strength is lower than a standard peel strength, a lower charging rate is set for the secondary battery assembly as compared to a standard secondary battery assembly that includes a positive electrode having the standard peel strength provided under standard conditions, and
    when the measured peel strength is higher than the standard peel strength, a higher charging rate is set for the secondary battery assembly as compared to the standard secondary battery assembly.

2. The method of producing a secondary battery according to claim 1, wherein the initial charging of the secondary battery assembly includes:
    emitting ultrasonic waves toward an interface between the positive electrode active material layer and the positive electrode current collector, and changing the charging rate according to a transmission intensity of the ultrasonic waves.

3. The method of producing a secondary battery according to claim 2, wherein the charging rate is reduced when the transmission intensity of the ultrasonic waves is equal to or less than a predetermined value.

4. The method of producing a secondary battery according to claim 1, wherein:

charging rate≤a×peel strength$^2$+b, and a>0, b=0.

5. The method of producing a secondary battery according to claim 4, wherein:

charging rate=a×peel strength$^2$+b−c, and c is a value that satisfies a×peel strength$^2$+b>c>0.

6. The method of producing a secondary battery according to claim 4, wherein:

charging rate={a×peel strength$^2$+b}×c', and c' is a value that satisfies 0<c'<1.

* * * * *